(12) United States Patent
Okaguchi et al.

(10) Patent No.: US 7,394,180 B2
(45) Date of Patent: Jul. 1, 2008

(54) OSCILLATOR CIRCUIT INCLUDING SURFACE ACOUSTIC WAVE SENSOR AND BIOSENSOR APPARATUS

(75) Inventors: Kenjiro Okaguchi, Kyoto-fu (JP); Koji Fujimoto, Otsu (JP); Michio Kadota, Kyoto (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 127 days.

(21) Appl. No.: 10/595,317

(22) PCT Filed: Sep. 8, 2004

(86) PCT No.: PCT/JP2004/013072

§ 371 (c)(1),
(2), (4) Date: Apr. 7, 2006

(87) PCT Pub. No.: WO2005/043150

PCT Pub. Date: May 12, 2005

(65) Prior Publication Data

US 2007/0252475 A1 Nov. 1, 2007

(30) Foreign Application Priority Data

Oct. 31, 2003 (JP) ............................. 2003-372207

(51) Int. Cl.
*H01L 41/09* (2006.01)
(52) U.S. Cl. .................... 310/317; 310/313 R; 331/155
(58) Field of Classification Search ............. 310/313 R, 310/317, 338; 73/32 R, 649, 664; 331/155
See application file for complete search history.

(56) References Cited

U.S. PATENT DOCUMENTS 6,314,791 B1 11/2001 Rapp et al.

(Continued)

FOREIGN PATENT DOCUMENTS

JP 02-60211 2/1990

(Continued)

OTHER PUBLICATIONS

Official communication issued in the counterpart Chinese Application No. 200480032329.0, mailed on May 25, 2007.

(Continued)

*Primary Examiner*—Thomas M Dougherty
(74) *Attorney, Agent, or Firm*—Keating & Bennett, LLP

(57) ABSTRACT

A surface-acoustic-wave-sensor-included oscillator circuit does not cause separation of an electrode film due to application of a bias voltage and can reliably accurate operate even if liquid is adhered thereto. The surface-acoustic-wave-sensor-included oscillator circuit includes interdigital electrode disposed on a piezoelectric substrate and a reaction film that is arranged so as to cover the interdigital electrodes and bound to a target substance or a binding material to be bound to the target substance. A surface acoustic wave sensor that is capable of detecting a bit of mass loading on the basis of a variation in frequency is connected as a resonator in the surface-acoustic-wave-sensor-included oscillator circuit. Direct-current cutting capacitors are connected in series to the surface acoustic wave sensor, and the direct-current cutting capacitors respectively define impedance matching circuits in the surface-acoustic-wave-sensor-included oscillator circuit.

7 Claims, 7 Drawing Sheets

U.S. PATENT DOCUMENTS 7,046,096 B2 * 5/2006 Kobayashi ............... 331/135
2004/0233008 A1 11/2004 Kobayashi

FOREIGN PATENT DOCUMENTS

| | | |
|---|---|---|
| JP | 02-164121 | 6/1990 |
| JP | 02-306706 | 12/1990 |
| JP | 04-148844 | 5/1992 |
| JP | 10-90270 | 4/1998 |
| JP | 2004-304766 | 10/2004 |
| WO | WO 99/21001 | 4/1999 |

OTHER PUBLICATIONS

International Search Report for PCT Application No. PCT/JP2004/013072, mailed Dec. 28, 2004.

Official communication issued in counterpart Chinese Application No. 200480032329.0, issued on Mar. 14, 2008.

* cited by examiner

US 7,394,180 B2

OSCILLATOR CIRCUIT INCLUDING SURFACE ACOUSTIC WAVE SENSOR AND BIOSENSOR APPARATUS

BACKGROUND OF THE INVENTION

1. Field of the Invention

The present invention relates to surface-acoustic-wave-sensor-included oscillator circuits including surface acoustic wave sensors, which are used as resonators, for use in, for example, biosensors or gas sensors. More particularly, the present invention relates to a surface-acoustic-wave-sensor-included oscillator circuits using a surface acoustic wave sensor that detects a target substance on the basis of a variation in frequency due to mass loading and to a biosensor apparatus using the surface-acoustic-wave-sensor-included oscillator circuit.

2. Description of the Related Art

Various surface acoustic wave sensors using surface acoustic wave devices have been proposed in order to detect various substances. For example, surface acoustic wave sensors for detecting biological materials, such as deoxyribonucleic acids (DNAs) or antibodies, have reaction films that react only to specific biological materials, such as DNAs or antibodies, on their surface acoustic wave devices. In such surface acoustic wave sensors, the DNAs or antibodies respond to the reaction films and are bound to the reaction films to load the mass on the surface acoustic wave devices. The presence or concentration of the DNAs or antibodies is detected on the basis of a variation in frequency due to the mass loading.

Japanese Unexamined Patent Application Publication No. 10-90270 (Patent Document 1) discloses an example of a surface acoustic wave sensor of this type. The surface acoustic wave sensor described in the related art is capable of detecting 2-methylisoborneol (2-MIB), which is a musty odor element contained in water. As shown in FIG. 11, a surface acoustic wave sensor 101 has interdigital electrodes 103 and 104 and a metal thin film 105 formed on a piezoelectric substrate 102. Amplifiers 106 and 107 are connected between the interdigital electrode 103 and the interdigital electrode 104. A mixer 108 is connected downstream of the interdigital electrode 104 at the output side and the amplifiers 106 and 107. The surface acoustic wave sensor 101 is structured such that an output is provided through the mixer 108.

In the surface acoustic wave sensor 101 described in the related art, an OVA-camphor complex is immobilized over the piezoelectric substrate 102. This OVA-camphor complex functions as a reaction film, and the 2-MIB is detected on the basis of a reaction of the 2-MIB to the OVA-camphor complex.

Specifically, the camphor-protein complex antigen, which has a structure similar to that of the 2-MIB being the musty odor element, is immobilized in the surface acoustic wave sensor 101. The surface acoustic wave sensor 101 is dipped in a solution to be measured, which contains an anti-2-MIB-antibody of a certain concentration specifically bound to the 2-MIB, and the 2-MIB whose concentration is unknown, in the solution, competitively reacts to the camphor-protein complex antigen. The amount of anti-2-MIB-angibody bound to the camphor-protein complex antigen immobilized over the surface acoustic wave sensor 101 is yielded on the basis of a variation in output level due to the mass loading on the surface acoustic wave sensor. A difference between the amount of anti-2-MIB-antigen bound to the camphor-protein complex antigen and the amount of the bound antibody when the 2-MIB does not exist is calculated to determine the concentration of the 2-MIB in the solution to be measured.

As described above, in the surface acoustic wave sensor of this type, a variation in mass is detected as a variation in frequency. Specifically, the surface acoustic wave sensor is included in the oscillator circuit as a resonator, and a variation in mass is detected on the basis of a variation in frequency of the oscillator circuit.

Exemplary oscillator circuits using surface acoustic wave devices as resonators are disclosed in Patent Documents 2 and 3. The oscillator circuits disclosed in Patent Documents 2 and 3 are used in radio systems, such as voltage controlled oscillator circuits or remote controllers. FIG. 12 is an exemplary circuit diagram of an oscillator circuit of this type.

An oscillator circuit 121 uses a surface acoustic wave device 122 as a resonator. In the oscillator circuit 121, the surface acoustic wave device 122 is a two-port surface acoustic wave resonator. A first port of the two-port surface acoustic wave resonator 122 is connected to the gate terminal of a field effect transistor (FET) 123. A second port of the two-port surface acoustic wave resonator 122 is connected to the drain terminal of the FET 123.

An oscillation output is provided through an output terminal 124 connected to the gate terminal of the FET 123.

The oscillator circuit 121 in FIG. 12 uses the surface acoustic wave device as a resonator, as in Patent Documents 2 and 3. However, such oscillator circuits are used in the radio systems, such as the voltage controlled oscillator circuits or the remote controllers, and are not used for detection of a target substance.

In addition, in the oscillator circuit 121 in FIG. 12, a several-V DC voltage corresponding to a bias voltage of the FET 123 is normally applied to the interdigital electrode portion of the surface acoustic wave device 122 connected to the FET 123.

When the surface acoustic wave sensor, such as the one disclosed in Japanese Unexamined Patent Application Publication No. 10-90270, is used in the oscillator circuit 121 in FIG. 12, the following problems are caused. The surface acoustic wave sensor is normally dipped in a liquid, such as body fluid or blood, in order to detect a target substance with the surface acoustic wave sensor. Accordingly, part of the liquid is adhered to the surface of the surface acoustic wave sensor. In addition, when the surface acoustic wave sensor is used, instead of the surface acoustic wave device 122 in the oscillator circuit 121 in FIG. 12, a DC bias voltage is applied to the interdigital electrode portion of the surface acoustic wave sensor, as described above. As a result, with the DC bias voltage being applied, dielectric breakdown is caused through the liquid adhered to the surface of the surface acoustic wave sensor to cause the electrode in the interdigital electrode portion to be separated.

In other words, since the use of the oscillator circuit 121 or the like with the surface acoustic wave sensor to be dipped in a liquid is not assumed, the surface acoustic wave sensor used in the oscillator circuit 121 is not proposed.

Patent Document 2: Japanese Unexamined Patent Application Publication No. 2-60211

Patent Document 3: Japanese Unexamined Patent Application Publication No. 2-164121

SUMMARY OF THE INVENTION

In order to resolve the above-described problems, preferred embodiments of the present invention provide a surface-acoustic-wave-sensor-included oscillator circuit that uses, as a resonator, a surface acoustic wave sensor that is capable of detecting a target substance on the basis of a variation in frequency caused by a variation in mass loading and that is unlikely to have a defect, such as electrode separation, due to application of the DC bias voltage and, therefore, is capable of stably operating. Preferred embodiments of the present invention also provide a biosensor apparatus including such a novel surface-acoustic-wave-sensor-included oscillator circuit.

A surface-acoustic-wave-sensor-included oscillator circuit has a piezoelectric substrate, an electrode arranged on the piezoelectric substrate to excite a surface acoustic wave, and a reaction film arranged on the piezoelectric substrate so as to cover the electrode for exciting the surface acoustic wave and bound to a target substance or a binding material to be bound to the target substance. A surface acoustic wave sensor that is capable of detecting a bit of mass loading on the basis of a variation in frequency is connected as a resonator in the surface-acoustic-wave-sensor-included oscillator circuit. The surface-acoustic-wave-sensor-included oscillator circuit preferably includes direct-current cutting capacitor connected in series to the surface acoustic wave sensor, and an impedance matching circuit includes the direct-current cutting capacitor.

According to a preferred embodiment of the surface-acoustic-wave-sensor-included oscillator circuit of the present invention, the impedance matching circuit includes an inductance element connected in series to the direct-current cutting capacitor, a first capacitor connected between one end of the inductance element and ground potential, and a second capacitor connected between the other end of the inductance element and the ground potential.

According to another preferred embodiment of the surface-acoustic-wave-sensor-included oscillator circuit of the present invention, the surface-acoustic-wave-sensor-included oscillator circuit further includes a resistor connected between a connection point between the surface acoustic wave sensor and the direct-current cutting capacitor and the ground potential.

According to yet another preferred embodiment of the surface-acoustic-wave-sensor-included oscillator circuit of the present invention, the surface acoustic wave sensor includes the two-port surface acoustic wave resonator.

According to still another preferred embodiment of the surface-acoustic-wave-sensor-included oscillator circuit of the present invention, the surface acoustic wave sensor including the two-port surface acoustic wave resonator has first and second ports. The surface-acoustic-wave-sensor-included oscillator circuit includes first and second direct-current cutting capacitors as the direct-current cutting capacitor. The surface-acoustic-wave-sensor-included oscillator circuit includes, as the impedance matching circuit, a first impedance matching circuit that has first and second terminals, the first terminal being connected to the first port, and includes the first direct-current cutting capacitor, and a second impedance matching circuit that has first and second terminals, the first terminal being connected to the second port, and includes the second direct-current cutting capacitor. The surface-acoustic-wave-sensor-included oscillator circuit further includes a transistor connected to the second terminal of the first impedance matching circuit and to the second terminal of the second impedance matching circuit.

According to further still another preferred embodiment of the surface-acoustic-wave-sensor-included oscillator circuit of the present invention, a field effect type transistor is used as the transistor.

A biosensor apparatus according to another preferred embodiment of the present invention includes the surface-acoustic-wave-sensor-included oscillator circuit structured according to the present invention.

In the surface-acoustic-wave-sensor-included oscillator circuit according to various preferred embodiments of the present invention, the surface acoustic wave sensor that is capable of detecting the mass loading on the basis of a variation in frequency is used as a resonator, the serial cutting capacitor is connected to the surface acoustic wave sensor, and the impedance matching circuit including the direct-current cutting capacitor is provided. Accordingly, even if the surface acoustic wave sensor is dipped in liquid, such as an aqueous solution, the direct-current cutting capacitor inhibits the DC bias current from being applied to the electrode portion. Hence, it is possible to prevent separation of the electrodes, etc., due to the DC bias voltage.

Since only connecting the direct-current cutting capacitor loses the impedance matching in circuit and causes a positive feedback, which is an amplitude condition for oscillation, not to exceed one, the surface-acoustic-wave-sensor-included oscillator circuit does not oscillate. However, the direct-current cutting capacitor also forms the impedance matching circuit in the surface-acoustic-wave-sensor-included oscillator circuit of various preferred embodiments of the present invention, so that stopping of the oscillation can be avoided. In other words, even if a bit of mass is loaded on the surface acoustic wave sensor, an oscillation output having the frequency varied in accordance with the mass loading can be surely yielded and, therefore, it is possible to reliably and precisely detect the mass loading with the surface acoustic wave sensor.

When the impedance matching circuit includes the inductance element connected in series to the direct-current cutting capacitor, the first capacitor connected between one end of the inductance element and ground potential, and the second capacitor connected between the other end of the inductance element and the ground potential, arbitrary movement on an impedance plane represented in a complex number, such as $Z=R+jX$, in a Smith chart, etc., is possible. Accordingly, the impedance matching can be easily attained independently of the impedance of the surface acoustic wave sensor and, therefore, the oscillation output in a wide band can be yielded.

When the surface-acoustic-wave-sensor-included oscillator circuit according to various preferred embodiments of the present invention further includes the resistor connected between the connection point between the surface acoustic wave sensor and the direct-current cutting capacitor and the ground potential, it is possible to effectively prevent the electrode fingers of the interdigital electrodes from being short-circuited due to the pyroelectric effect.

When the surface acoustic wave sensor uses the two-port surface acoustic wave resonator in the surface-acoustic-wave-sensor-included oscillator circuit according to a preferred embodiment of the present invention, lengthening the interval between the two reverse-phased SAW modes, which are called zeroth and primary modes (or primary and secondary modes) and which have a higher excitation strength, broadens the passband. As a result, it is possible to improve the detectivity of the surface acoustic wave sensor.

When the surface acoustic wave sensor including the two-port surface acoustic wave resonator has first and second ports, the surface-acoustic-wave-sensor-included oscillator circuit includes first and second direct-current cutting capacitors as the direct-current cutting capacitor, the surface-acoustic-wave-sensor-included oscillator circuit includes, as the impedance matching circuit, first and second impedance matching circuits, and the first terminal of the first impedance matching circuit is connected to the first port, the second terminal thereof is connected to the transistor, the first terminal of the second impedance matching circuit is connected to the second port, and the second terminal thereof is connected to the transistor, the first and second impedance matching circuits are connected to the first and second ports, respectively, of the two-port surface acoustic wave resonator. Accordingly, the impedance matching with the transistor can be satisfactorily achieved and the oscillation conditions can be reliably satisfied. Hence, it is possible to cause the surface-acoustic-wave-sensor-included oscillator circuit including the surface acoustic wave sensor using the two-port surface acoustic wave resonator to operate more reliably.

The use of the field effect transistor as the transistor is suitable for a surface acoustic wave sensor having a relatively high impedance.

Since the biosensor apparatus according to a preferred embodiment of the present invention includes the surface-acoustic-wave-sensor-included oscillator circuit structured according to various other preferred embodiments of the present invention, it is possible to reliably and accurately detect a minute target substance on the basis of a variation in oscillation frequency.

Other features, elements, steps, characteristics and advantages of the present invention will become more apparent from the detailed description of preferred embodiments thereof with reference to the attached drawings.

BRIEF DESCRIPTION OF THE DRAWINGS

FIGS. 2A to 2D illustrate measurement principle of a surface acoustic wave sensor according to a preferred embodiment of the present invention wherein FIG. 2A is a cross-sectional front view schematically showing a state where a target substance does not exist in liquid, FIG. 2B illustrates variations in frequency where the target substance does not exist in the liquid; FIG. 2C is a cross-sectional front view schematically showing a state where the target substance exists in liquid, and FIG. 2D illustrates variations in frequency where the target substance exists in the liquid.

DETAILED DESCRIPTION OF PREFERRED EMBODIMENTS

Preferred embodiments of the present invention will be described with reference to the attached drawings.

FIGS. 2A to 2D illustrate measurement principles of a surface acoustic wave sensor used in a surface-acoustic-wave-sensor-included oscillator circuit according to a preferred embodiment of the present invention.

A surface acoustic wave sensor 1 according to the present preferred embodiment preferably utilizes a shear horizontal (SH) surface acoustic waves and has a rotated Y-cut $LiTaO_3$ substrate 2 having an Euler angle (0°, 0° to 18°, 0°±5) or (0°, 58° to 180°, 0°±5°). Interdigital electrodes 3 are formed on the $LiTaO_3$ substrate 2 as electrodes for exciting a surface acoustic wave. The interdigital electrodes 3 are preferably made of Au. The interdigital electrodes 3 preferably have a film thickness of about 0.8% to about 9.5% normalized with the wavelength of the surface acoustic wave. An $SiO_2$ dielectric film is formed on the Au electrodes.

A reaction film 4 is formed over the $LiTaO_3$ substrate. The reaction film 4 is made of an appropriate material that is bound to a target substance or a binding material to be bound to the target substance.

Figure 2A:
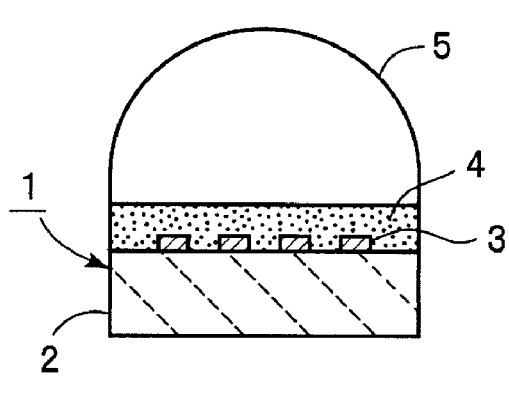

If the surface acoustic wave sensor 1 is dipped in, for example, a liquid 5 that does not contain the target substance, the liquid 5 comes in contact with the reaction film 4, as shown in FIG. 2A. Although the target substance does not exist in the liquid 5 in FIG. 2A, the liquid 5 comes in contact with the reaction film 4 and the surface where the interdigital electrodes 3 are formed on the $LiTaO_3$ substrate 2 is mass-loaded. Accordingly, as shown in FIG. 2B, the frequency decreases in a manner such that a frequency characteristic A before the surface acoustic wave sensor 1 is dipped in the liquid 5 is changed to a frequency characteristic B after the surface acoustic wave sensor 1 is dipped in the liquid 5. However, the amount of the variation in frequency is relatively small in this case.

Figure 2C:
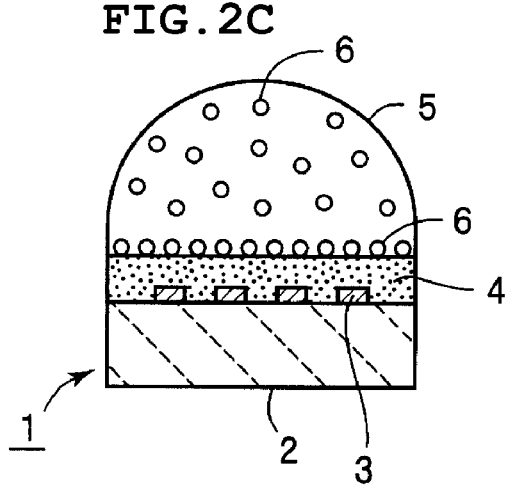
Figure 2B:
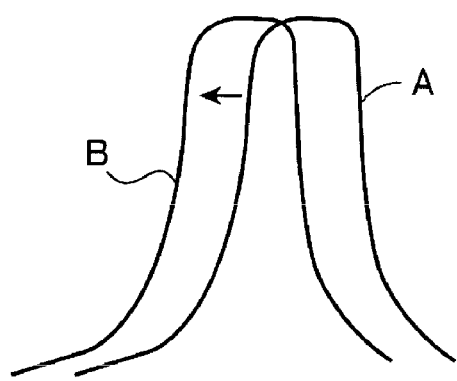
Figure 2D:
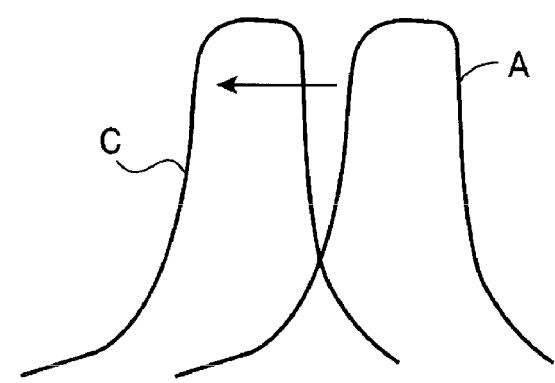

In contrast, if the surface acoustic wave sensor 1 is dipped in the liquid 5 that contains a target substance 6, as shown in FIG. 2C, the target substance 6 is bound to the reaction film 4. Hence, the surface where the interdigital electrodes 3 are formed on the $LiTaO_3$ substrate 2 is mass-loaded due to the target substance 6 bound to the surface of the reaction film 4, in addition to an increase in mass on the surface due to the liquid 5.

If the target substance 6 exists in the liquid 5, the target substance 6 responds to the reaction film 4 and is bound to the surface of the reaction film 4. As a result, the mass loading of the target substance 6 increases an effect on the SH surface acoustic wave excited on the surface of the $LiTaO_3$ substrate 2 and, therefore, it is possible to detect the presence of the target substance on the basis of a variation in frequency.

According to various preferred embodiments of the present invention, the shape of the interdigital electrodes of the surface acoustic wave sensor 1, which has the principle described above and which is effectively used, is not restricted. A one-port surface acoustic wave resonator having reflectors at both sides of one interdigital electrode in the direction at which the surface acoustic wave is propagated may be used or a two-port surface acoustic wave resonator shown in FIG. 3 may be used.

Figure 3:
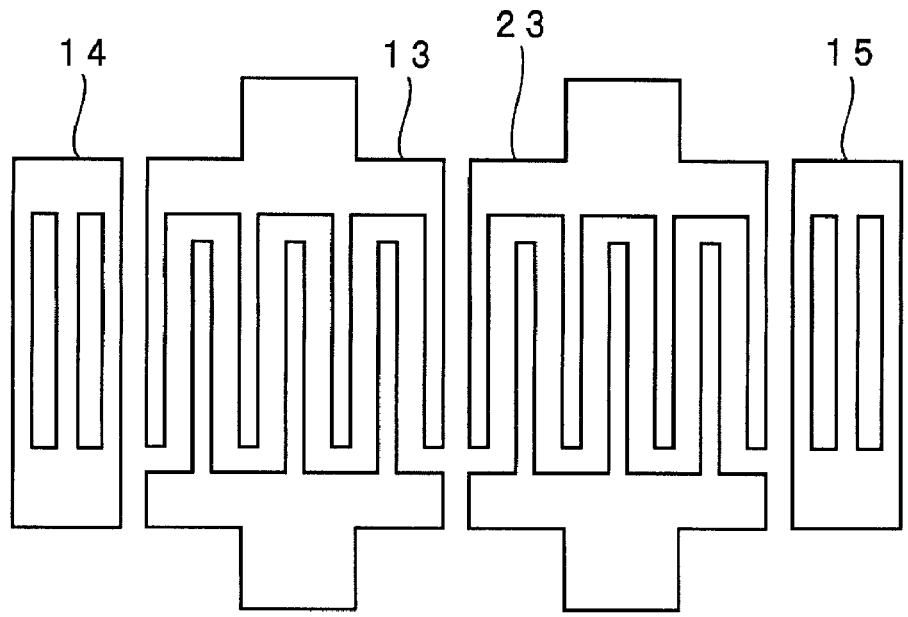
FIG. 3 is a plan view schematically showing the electrode structure of a two-port surface acoustic wave resonator used in a preferred embodiment of the present invention.

FIG. 3 is a plan view schematically showing the electrode structure of a two-port surface acoustic wave resonator. In the two-port surface acoustic wave resonator in FIG. 3, interdigital electrodes 13 and 23 are arranged adjacently to each other in the propagation direction of the surface acoustic wave, and reflectors 14 and 15 are arranged at both sides of an area where the interdigital electrodes 13 and 23 are provided in the propagation direction of the surface acoustic wave.

Next, a surface-acoustic-wave-sensor-included oscillator circuit according to a preferred embodiment of the present invention will be described with reference to FIG. 1.

Figure 1:
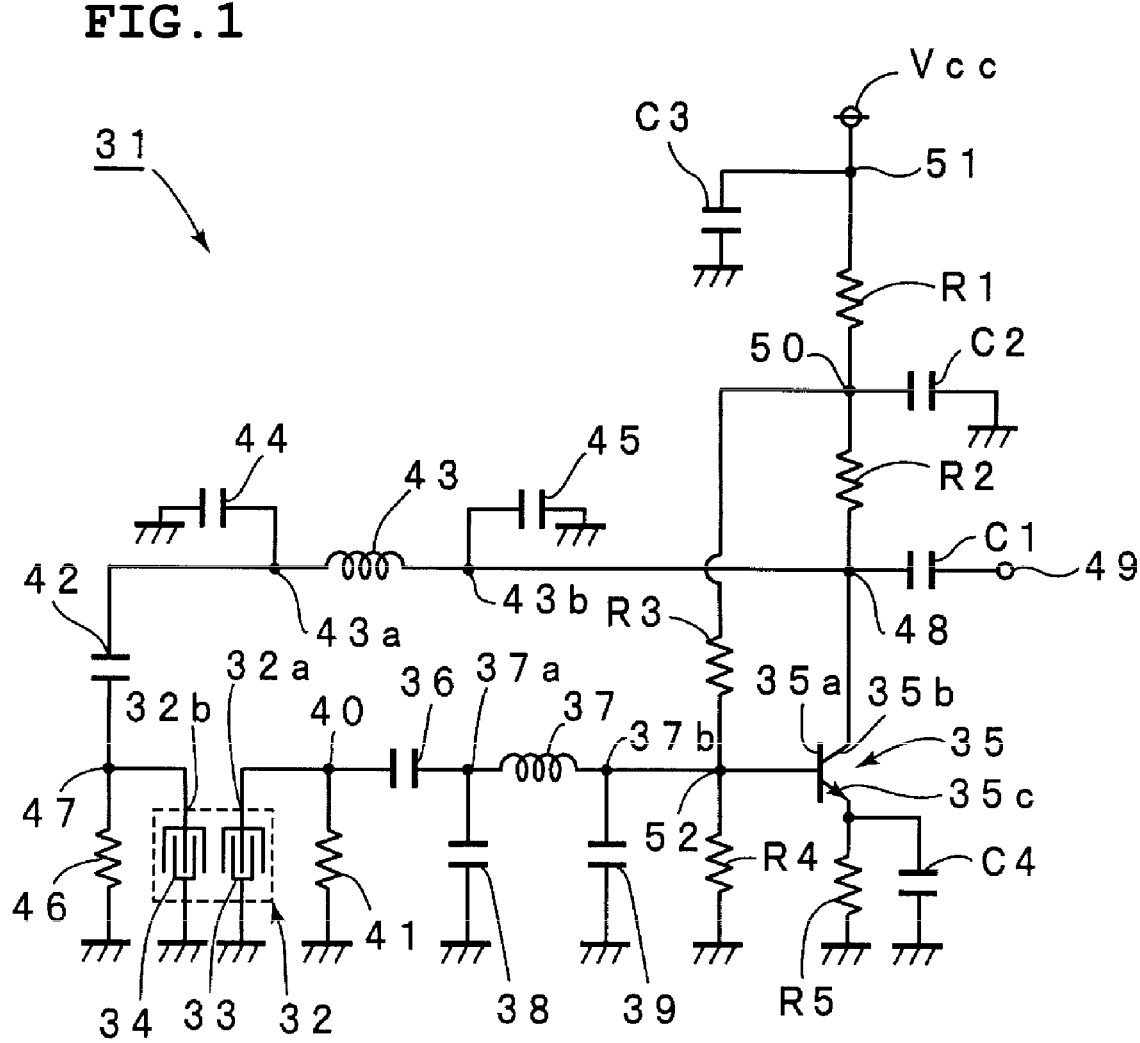
FIG. 1 is a circuit diagram of a surface-acoustic-wave-sensor-included oscillator circuit according to a preferred embodiment of the present invention.

As shown in FIG. 1, a surface-acoustic-wave-sensor-included oscillator circuit 31 according to a preferred embodiment includes a surface acoustic wave sensor 32 performing the measurement according to the above-described principle. The surface acoustic wave sensor 32 includes a two-port surface acoustic wave resonator including first and second interdigital electrodes 33 and 34, as schematically shown in FIG. 1. Accordingly, the surface acoustic wave sensor 32 has first and second ports 32a and 32b.

The surface acoustic wave sensor 32 schematically shown in FIG. 1 is structured in a manner similar to that of the surface acoustic wave sensor 1. That is, a reaction film is formed so as to cover the interdigital electrodes 33 and 34.

In addition, as shown in FIG. 1, the first port 32a is connected to a base terminal 35a of a transistor 35. A first direct-current cutting capacitor 36 and an inductance element 37 are connected in series between the first port 32a and the base terminal 35a. The inductance element 37 is connected toward the base terminal 35a. A capacitor element 38 is connected between a connection point 37a at one side of the inductance element 37 and the ground potential, and a capacitor element 39 is connected between a connection point 37b at the other side of the inductance element 37 and the ground potential. According to this preferred embodiment, a π-shaped filter portion including the inductance element 37 and the capacitor elements 38 and 39 and the first direct-current cutting capacitor 36 define a first impedance matching circuit. The first impedance matching circuit is structured so that an output impedance through the first port 32a is matched to an input impedance into the base terminal 35a of the transistor 35.

A resistor 41 is connected between the connection point 40 between the first port 32a and the first direct-current cutting capacitor 36 and the ground potential. The resistor 41 is provided in order to prevent the interdigital electrodes 32 and 33 from being short-circuited due to pyroelectric effect. Accordingly, the resistance of the resistor 41 is set so as to achieve this effect.

The second port 32b of the surface acoustic wave sensor 32 is connected to a collector terminal 35b of the transistor 35 via a second direct-current cutting capacitor 42 and an inductance element 43, which are connected in series to each other. The second direct-current cutting capacitor 42 is provided in order to prevent a DC bias voltage from being applied to the interdigital electrode 34. The inductance element 43 is connected toward the collector terminal 35b of the transistor 35. A capacitor element 44 is connected between a connection point 43a at one side of the inductance element 43 and the ground potential, and a capacitor element 45 is connected between a connection point 43b at the other side of the inductance element 43 and the ground potential. The inductance element 43, the capacitor elements 44 and 45, and the second direct-current cutting capacitor 42 form a second impedance matching circuit.

Accordingly, in the surface acoustic wave sensor 32, the first port 32a is connected to the transistor 35 via the first impedance matching circuit and the second port 32b is connected to the transistor 35 via the second impedance matching circuit.

Also at the side of the second port 32b, a resistor 46 is connected between the connection point 47 between the second port 32b and the second direct-current cutting capacitor 42 and the ground potential in order to prevent the interdigital electrode 34 from being short-circuited due to the pyroelectric effect.

The connection point 48 between the second impedance matching circuit and the collector terminal 35b of the transistor 35 is connected to an output terminal 49 via a capacitor C1. Resistors R1 and R2, which are connected in series to each other, are connected between the connection point 48 and a power supply voltage Vcc. The connection point 50 between the resistors R1 and R2 is grounded via a capacitor C2. The connection point 51 between the power supply voltage Vcc and the resistor R1 is grounded via a capacitor C3.

Resistors R3 and R4, which are connected in series to each other, are connected between the connection point 50 and the ground potential. The connection point 52 between the resistors R3 and R4 is connected to an output end of the first impedance matching circuit. A resistor R5 is connected between an emitter terminal 35c of the transistor 35 and the ground potential. A capacitor C4 is connected in parallel to the resistor R5.

Figure 4:
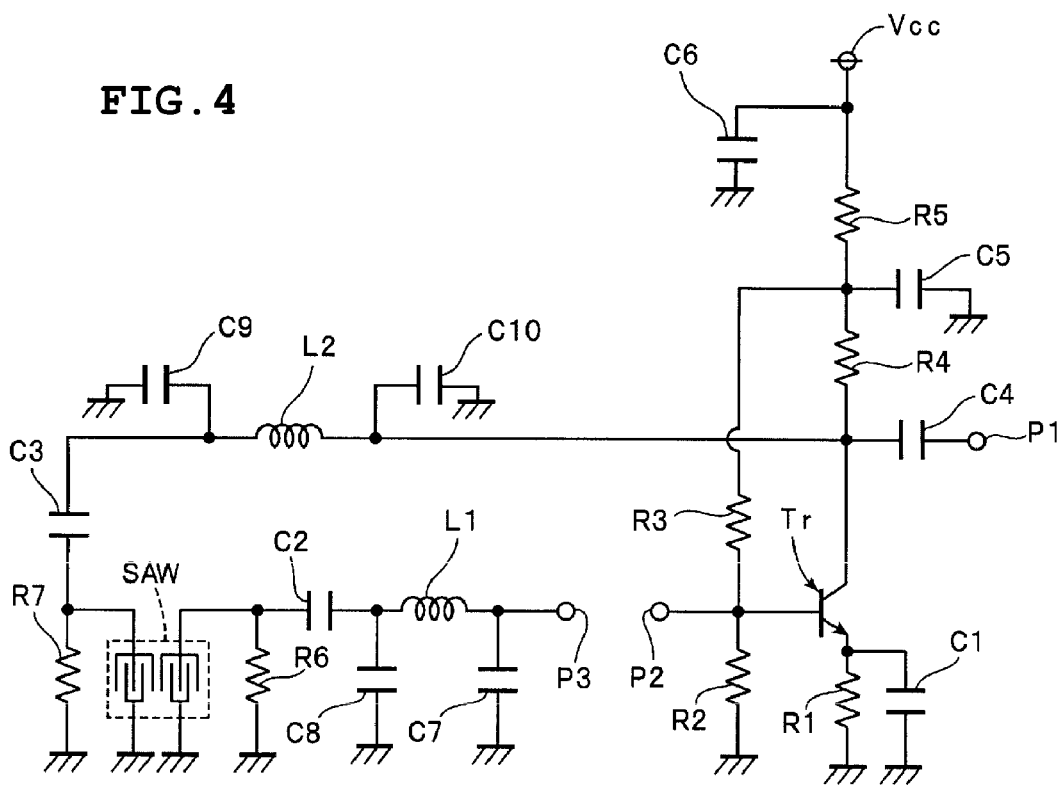
FIG. 4 is a circuit diagram of a modification of the surface-acoustic-wave-sensor-included oscillator circuit in FIG. 1, for illustrating oscillation conditions.

A circuit according to a modification of the present preferred embodiment, shown in FIG. 4, is examined in order to consider oscillation conditions in the surface-acoustic-wave-sensor-included oscillator circuit shown in FIG. 1. A circuit in FIG. 4 forms an open loop circuit in which the surface-acoustic-wave-sensor-included oscillator circuit in FIG. 1 has ports P1 to P3. The oscillation conditions of the surface-acoustic-wave-sensor-included oscillator circuit must satisfy the following Equations (1) and (2).

$$|S32| \geqq 0 \text{ (dB)} \quad (1)$$

$$\angle S32 = 360 \times n \text{(deg) where } n \text{ denotes an integer} \quad (2)$$

Equation (1) represents an amplitude condition and Equation (2) represents a phase condition. Consequently, the loop gain must be greater than or equal to 0 dB and the loop phase difference must be an integral multiple of 360 degrees in order to oscillate the surface-acoustic-wave-sensor-included oscillator circuit. In the circuit according to the modification, the port P1 is connected to a frequency counter of a 50-Ω system for measuring the oscillation frequency. Accordingly, the output impedance of the surface-acoustic-wave-sensor-included oscillator circuit is set to 50 Ω.

Figure 5:
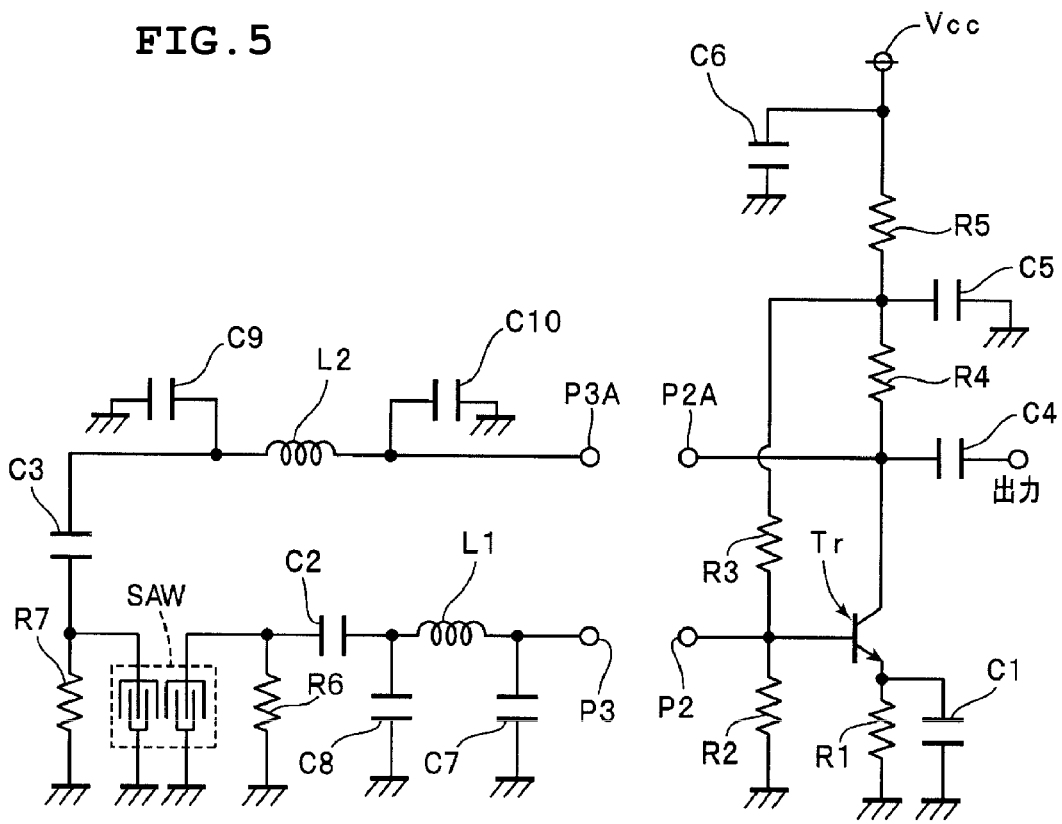
FIG. 5 is a circuit diagram of another modification of the surface-acoustic-wave-sensor-included oscillator circuit in FIG. 1, for illustrating the oscillation conditions.

A circuit including an oscillator system circuit portion and an amplifier system circuit portion, which result from separation of the circuit in FIG. 1, is shown in FIG. 5. When the impedance when the amplifier circuit portion is viewed from ports P2 and P2A is 50 Ω, it can be assumed that the reflection from each port is reduced and the loop gain is increased as the impedance when the oscillator system circuit portion is viewed from ports P3 and P3A is approximated to 50 Ω.

Figure 6:
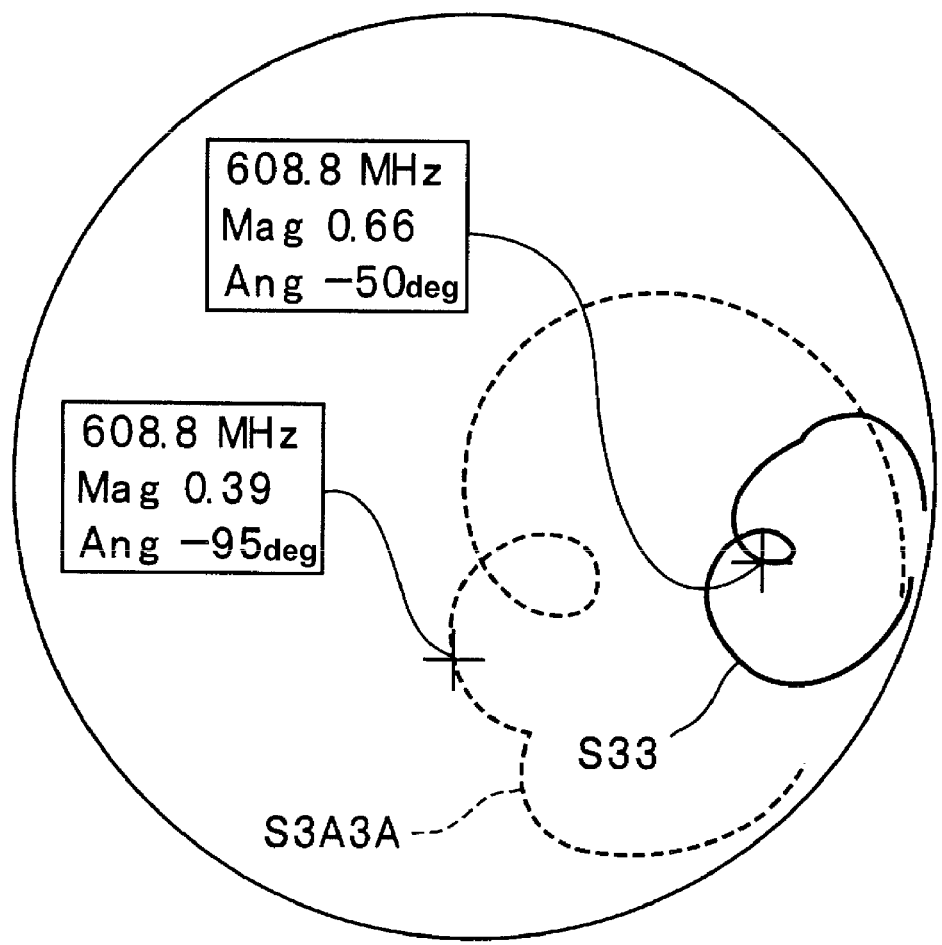
FIG. 6 illustrates the reflection coefficients of port 3 and 3A when a SAW filter shown in FIG. 8 is used and a resonator system circuit portion is set so as to have the settings shown in Table 1 in the circuit in FIG. 5.
Figure 8:
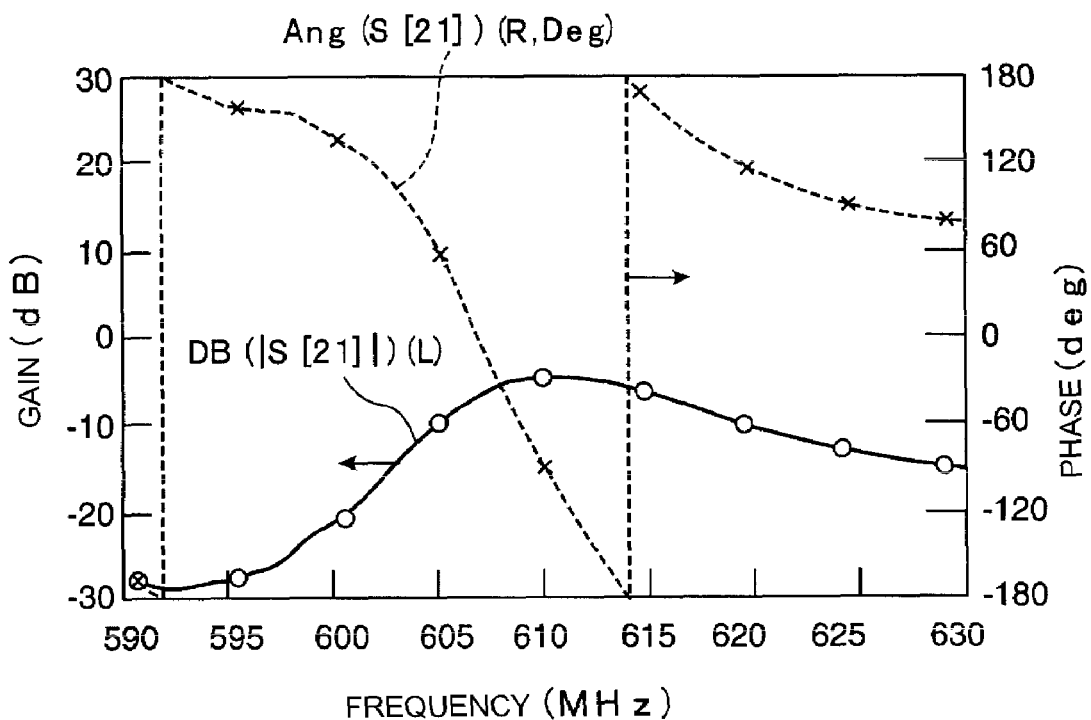
FIG. 8 shows examples of the characteristics of the SAW filter.

When a surface acoustic wave (SAW) filter having characteristics shown in FIG. 8 is used and the elements in the oscillator system circuit portion have values shown in Table 1, in the circuit shown in FIG. 5, the reflection coefficients corresponding to the port P3 and the port P3A are shown in FIG. 6.

TABLE 1

Values of Elements with Characteristics in FIG. 6

| L1 | 15 nH |
|----|-------|
| L2 | 15 nH |
| C2 | 18 pF |
| C3 | 18 pF |
| C7 | N. C |
| C8 | N. C |
| C9 | N. C |
| C10 | N. C |
| R6 | 100 kΩ |
| R7 | 100 kΩ |

N. C denotes non connection.

As apparent from characteristics of S33 and S3A3A shown in FIG. 6, the S3A3A has a characteristic close to 50 Ω while the S33 has a characteristic considerably shifted from 50 Ω.

Figure 7:
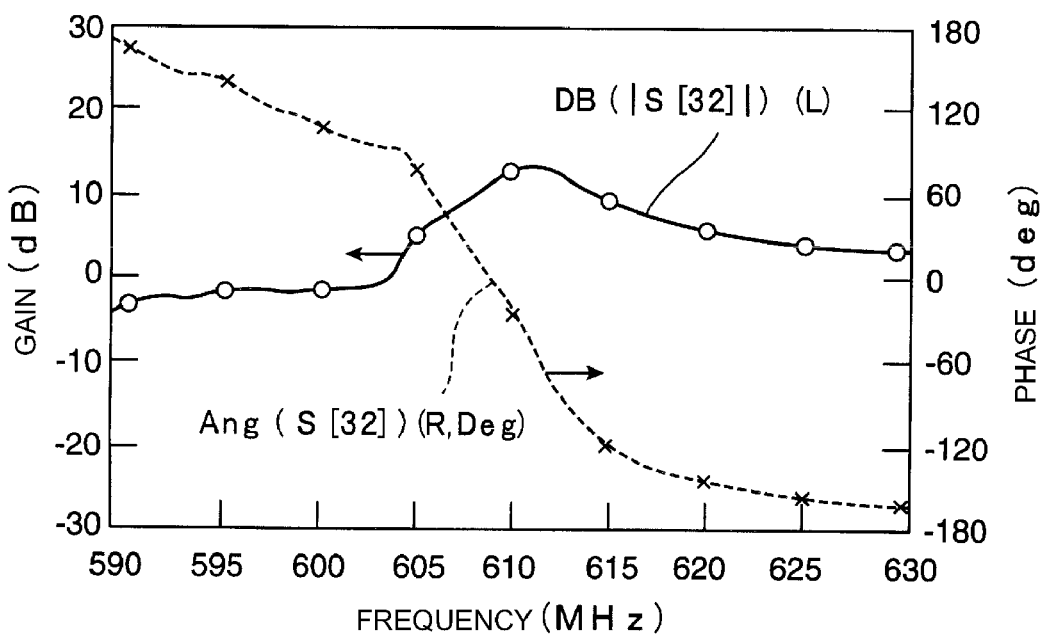
FIG. 7 shows amplitude and phase conditions of S32 when a port 2A is connected to a port 3A to form the circuit shown in FIG. 4.

When the port P2A is connected to the port P3A to form the circuit shown in FIG. 4 if the values of the elements are set so as to have the characteristics shown in FIG. 6, as shown in Table 1, S32 has amplitude and phase characteristics shown in FIG. 7. As apparent from FIG. 7, if the amplitude characteristic has a gain greater than zero with the phase characteristic being equal to zero, the oscillation conditions are satisfied. In order to improve the impedance matching in the oscillator system circuit portion, capacitors C7, C8, C9, and C10 of the oscillator system circuit portion should preferably be added. The addition of the capacitors makes the amplitude characteristic with the phase characteristic of S32 being zero greater than zero and, therefore, it is possible to sufficiently satisfy the oscillation conditions.

Consequently, the values of the elements in an impedance matching circuit including an inductance L1 and capacitors C2, C7, and C8 and in an impedance matching circuit including an inductance L2 and capacitors C3, C9, and C10 should be set such that the impedance of the oscillator system circuit portion is matched to the impedance of the amplifier system circuit portion as much as possible with the above structure.

In the surface-acoustic-wave-sensor-included oscillator circuit 31 according to this preferred embodiment, the resonant frequency of the surface acoustic wave sensor 32 is varied when a bit of mass is loaded on the surface acoustic wave sensor 32 due to the presence of the target substance. As a result, the oscillation frequency output through the output terminal 49 of the surface-acoustic-wave-sensor-included oscillator circuit 31 is varied and, thus, it becomes possible to detect the target substance. In this case, it is possible to surely prevent the DC bias voltage, described above, from being applied to the interdigital electrodes 33 and 34 owing to the first and second direct-current cutting capacitors 36 and 42. Hence, it is unlikely to short-circuit the interdigital electrodes 33 and 34 due to the application of the DC bias voltage and the electrode film is unlikely to separate from the substrate.

Although only connecting the direct-current cutting capacitor in series possibly loses the impedance matching and does not satisfy the oscillation conditions, the first and second direct-current cutting capacitor 36 and 42 are connected so as to define the first and second impedance matching circuits, described above, in this preferred embodiment. In other words, since the electrostatic capacitances of the first and second direct-current cutting capacitors 36 and 42 are set so as to define the first and second impedance matching circuits, the oscillation conditions are surely satisfied and the oscillation is unlikely to stop.

Hence, in the surface-acoustic-wave-sensor-included oscillator circuit 31 according to this preferred embodiment, the separation of the electrode film, etc. due to the application of the DC bias voltage is unlikely to occur. In addition, the oscillation conditions are surely satisfied even when the binding of the target substance, such as protein, to the surface of the surface acoustic wave sensor varies the oscillation frequency. Accordingly, it is possible to detect the target substance without fail.

Consequently, the surface-acoustic-wave-sensor-included oscillator circuit 31 according to the present preferred embodiment is preferably applicable to, for example, a biosensor apparatus for detecting a target substance, such as protein in biological fluid.

Although the transistor 35 is preferably used in the above-described preferred embodiment, a field effect type transistor may be used instead of the transistor 35. Such a case is suitable for a surface acoustic wave sensor having a relatively high impedance.

Next, specific experimental examples will be described.

Figure 12:
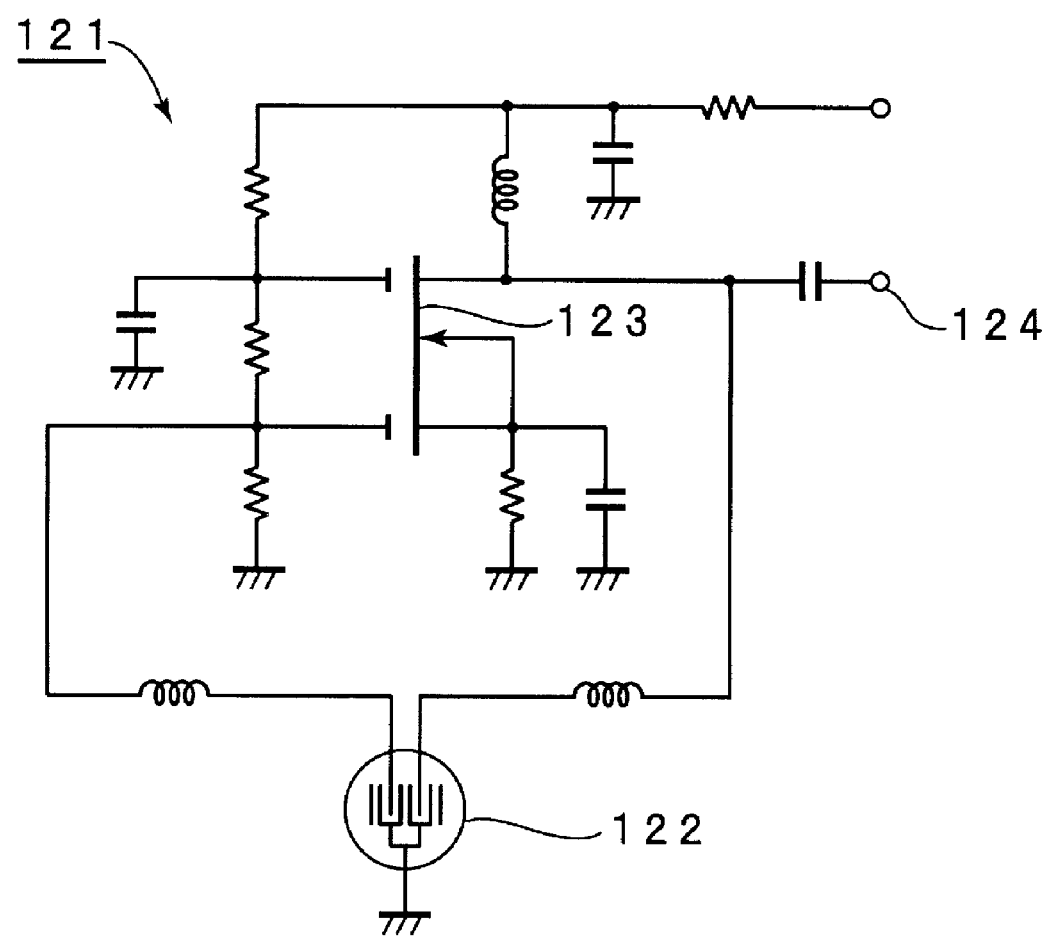
FIG. 12 is a circuit diagram of an oscillator circuit using the surface acoustic wave resonator, in a related art.

The surface acoustic wave sensor 32 including the two-port surface acoustic wave resonator was used to form the surface-acoustic-wave-sensor-included oscillator circuit 31 shown in FIG. 1. For comparison, the same surface acoustic wave sensor was used to form the oscillator circuit 121 shown in FIG. 12.

The electrode fingers of the first and second interdigital electrodes in the used surface acoustic wave sensor have a logarithm of 12 and have a wavelength of about 5.8 μm. In addition, anti-albumin was bound to a cyano-alkane film, serving as a reaction film, on the interdigital electrodes.

Figure 9:
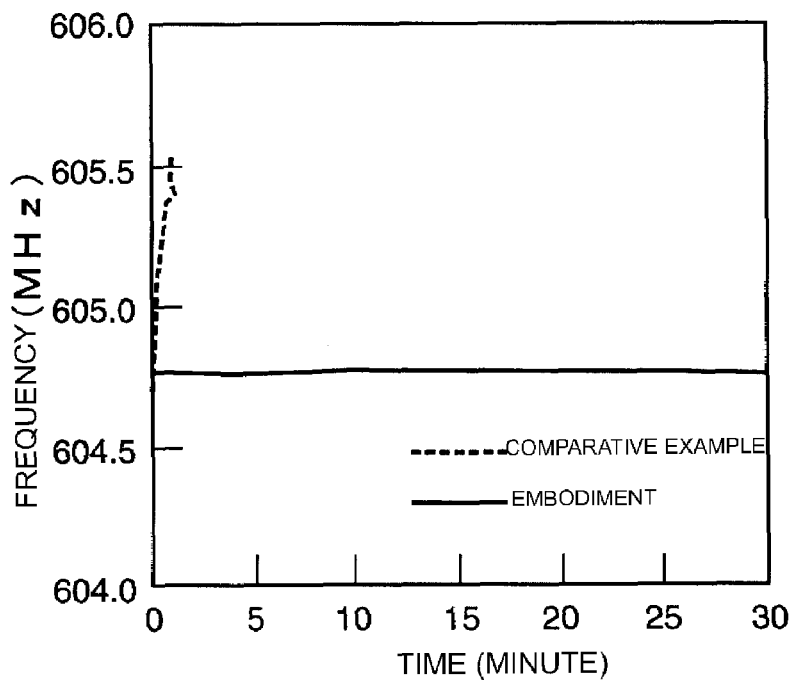
FIG. 9 shows variations in oscillation frequency when liquid is adhered to the surfaces of the surface acoustic wave sensors in the surface-acoustic-wave-sensor-included oscillator circuits according to a preferred embodiment of the present invention and in a comparative example.
Figure 10:
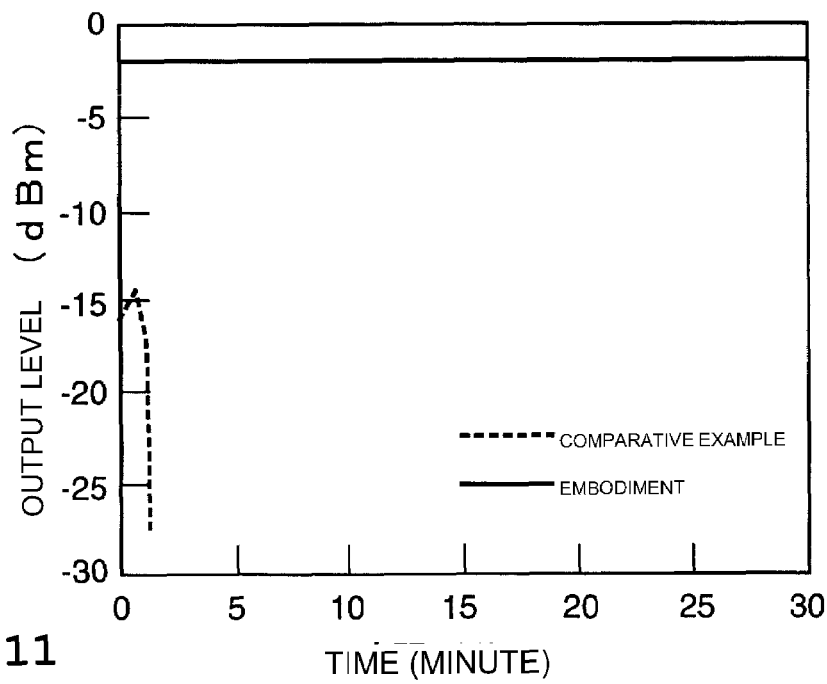
FIG. 10 shows variations in output level when liquid is adhered to the surfaces of the surface acoustic wave sensors in the surface-acoustic-wave-sensor-included oscillator circuits according to a preferred embodiment of the present invention and in the comparative example.
Figure 11:
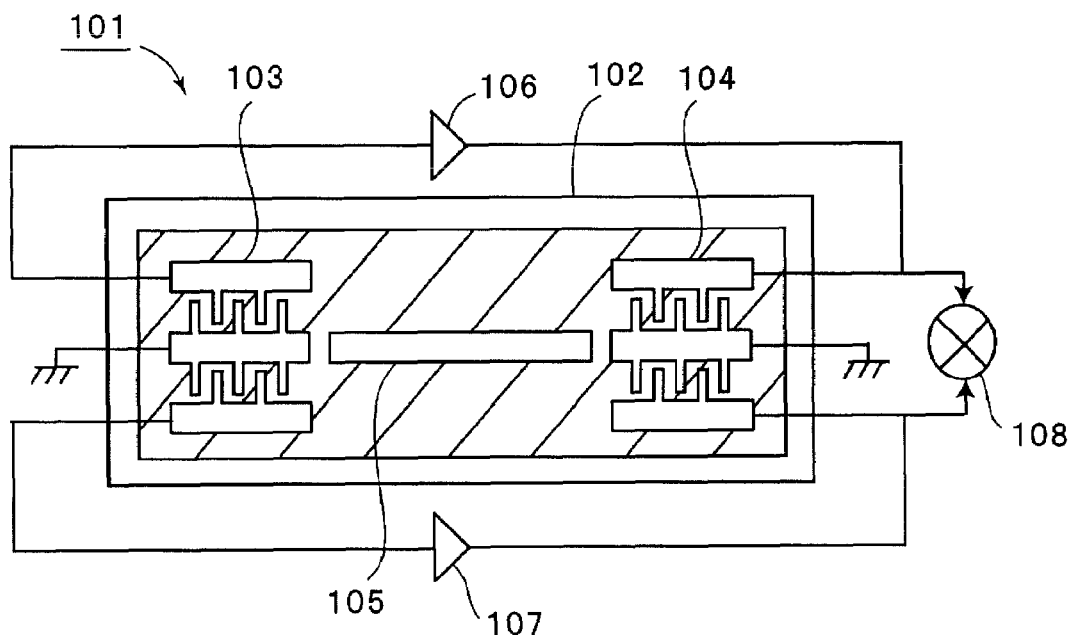
FIG. 11 is a plan view schematically showing an example of a surface acoustic wave sensor in a related art.

Variations in the output frequency and in the output level when physiological saline solution, as an aqueous solution containing a target substance, is adhered to the surfaces of the surface acoustic wave sensors in the oscillation circuits according to the above-described preferred embodiment and in the comparative example are shown in FIGS. 9 and 10. In FIGS. 9 and 10, broken lines show results of the oscillation circuit in the comparative example while solid lines show results of the surface-acoustic-wave-sensor-included oscillator circuit according to the preferred embodiments.

As apparent from FIGS. 9 and 10, when the oscillation circuit in the comparative example was used, the oscillation frequency and the output level were greatly varied for a short time due to the adhesion of the liquid and the oscillation quickly stopped. Accordingly, it is not possible to detect the target substance by using the surface acoustic wave sensor. In contrast, in the surface-acoustic-wave-sensor-included oscillator circuit according to the above-described preferred embodiment, it is possible to yield the stable frequency and output level and to surely and stably detect a variation in frequency due to the adhesion of the liquid containing the target substance.

While preferred embodiments of the present invention have been described above, it is to be understood that variations and modifications will be apparent to those skilled in the art without departing the scope and spirit of the present invention. The scope of the present invention, therefore, is to be determined solely by the following claims.

The invention claimed is:

1. A surface-acoustic-wave-sensor-included oscillator circuit comprising:
    a piezoelectric substrate;
    an electrode arranged on the piezoelectric substrate so as to excite a surface acoustic wave;
    a reaction film arranged on the piezoelectric substrate so as to cover the electrode and so as to excite a surface acoustic wave, the reaction film being bound to a target substance or a binding material to be bound to the target substance; and a surface acoustic wave sensor that is capable of detecting a bit of mass loading on the basis of a variation in frequency being connected as a resonator; wherein the surface-acoustic-wave-sensor-included oscillator circuit includes a direct-current cutting capacitor connected in series to the surface acoustic wave sensor, and an impedance matching circuit including the direct-current cutting capacitor is provided in the surface-acoustic-wave-sensor-included oscillator circuit.

2. The surface-acoustic-wave-sensor-included oscillator circuit according to claim 1, wherein the impedance matching circuit includes an inductance element connected in series to the direct-current cutting capacitor, a first capacitor connected between one end of the inductance element and ground potential, and a second capacitor connected between the other end of the inductance element and the ground potential.

3. The surface-acoustic-wave-sensor-included oscillator circuit according to claim 1, further comprising a resistor connected between a connection point between the surface acoustic wave sensor and the direct-current cutting capacitor and the ground potential.

4. The surface-acoustic-wave-sensor-included oscillator circuit according to claim 1, wherein the surface acoustic wave sensor includes a two-port surface acoustic wave resonator.

5. The surface-acoustic-wave-sensor-included oscillator circuit according to claim 4, wherein the surface acoustic wave sensor has first and second ports, the surface-acoustic-wave-sensor-included oscillator circuit includes first and second direct-current cutting capacitors as the direct-current cutting capacitor, and the surface-acoustic-wave-sensor-included oscillator circuit includes, as the impedance matching circuit, a first impedance matching circuit that has first and second terminals, the first terminal being connected to the first port, and includes the first direct-current cutting capacitor, and a second impedance matching circuit that has first and second terminals, the first terminal being connected to the second port, and includes the second direct-current cutting capacitor, and wherein the surface-acoustic-wave-sensor-included oscillator circuit further includes a transistor connected to the second terminal of the first impedance matching circuit and to the second terminal of the second impedance matching circuit.

6. The surface-acoustic-wave-sensor-included oscillator circuit according to claim 5, wherein the transistor is a field effect type transistor.

7. A biosensor apparatus comprising the surface-acoustic-wave-sensor-included oscillator circuit according to claim 1.

* * * * *